US005800814A

United States Patent [19]
Fusek et al.

[11] Patent Number: 5,800,814
[45] Date of Patent: Sep. 1, 1998

[54] METHOD FOR INHIBITION OF BREAST TUMOR GROWTH

[75] Inventors: Martin Fusek, Oklahoma City, Okla.; Vaclav Vetvicka, Louisville, Ky.

[73] Assignee: Oklahoma Medical Research Foundation, Oklahoma City, Okla.

[21] Appl. No.: 232,997

[22] Filed: Apr. 22, 1994

[51] Int. Cl.[6] .................... A61K 39/395; A61K 38/00
[52] U.S. Cl. ........................ 424/133.1; 530/387.1; 530/387.9; 530/386.26; 530/288.85; 530/324; 514/44; 514/12; 435/240.27; 424/145.1; 424/185.1
[58] Field of Search ................. 530/387.1, 387.9, 530/388.26, 388.85, 324; 514/44, 12; 435/240.27; 424/145.1, 185.1, 133.1

[56] References Cited

PUBLICATIONS

Baldwin, E.T., "Crystal Structures of Native and Inhibited Forms of Human Cathepsin D: Implications for lysosomal Targeting and Drug Design," *Proc. Natl. Acad. Sci. USA*, vol. 90, pp. 6796–6800 (1993).

BarRett, A.J. "Purification of Isoenzymes from Human and Chicken Liver," *Biochem J.*, vol. 117, pp. 601–607 (1970).

Bond, J.S., et al., "Intracellular Proteases," *Ann. Rev. Biochem.*, vol. 56, pp. 333–364 (1987).

Cavailles, V., et al., "Cathepsin D Gene is Controlled by a Mixed Promoter, and Estrogens Stimulate only TATA–Dependent Transcription in Breast Cancer Cells," *Proc. Natl. Acad. Sci. USA*, vol. 90, pp. 203–207 (1993).

Clackson, T., et al., "Making Antibody Fragments Using Phage Display Libraries," *Nature*, vol. 352, pp. 624–628 (1991).

Creek, K.E., et al., "The Role of the Phosphomannosyl Receptor in the Transport of Acid Hydrolases to Lysosomes," *Lysosomes in Biology and Pathology*, pp. 63–82 (1984).

Daugherty, B.L., et al., "Polymerase Chain Reaction Facilitates the Cloning, CDR–grafting, and Rapid Expression of a Murine Monoclonal Antibody Directed Against the CD18 Component of Leukocyte Integrins," *Nucleic Acids Res.*, vol. 19, No. 9, pp. 2471–2476 (1991).

Diment, S., et al., "Cathespin D is Membrane–Associated in Macrophase Endosomes," *J. Biological Chemistry*, vol. 263, No. 14, pp. 6901–6907 (1988).

Eddy, A., et al., "The Distribution of the CR3 Receptor on Human Cells and Tissue as Revealed by a mOnoclonal Antibody," *Clinical Immunology and Immunopathology*, vol. 31, pp. 371–389 (1984).

Elangovan, S., et al., "Progesterone and Estrogen Control of Rates of Synthesis of Uterine Cathespin D," *J. Biological Chemistry*, vol. 255, No. 15, pp. 7474–7479 (1980).

Fusek, Martin, et al., "Mitogenic function of human procathepsin D: the role of the propeptide", *Biochem., J., vol.* 303:775–780 (1994).

Glickman, J.N., et al., "Manose 6–Phosphate–Independent Targeting of Lysosomal Enzymemes in I–Cell Disease B Lymophoblasts," *J. Cell Biology*, vol. 123, No. 1, pp. 99–108 (1993).

Grassel, S. et al., "Human Cathepsin D Precursor is Associated with a 60 kDa Glycosylated Polypeptide," *Biochemical and Biophysical Research Communications*, vol. 182, No. 1, pp. 276–282 (1992).

Grinstein S., et al., "Chemoattractant–Induced Tyrosine Phosphorylation and Activation of Microtuble–Associated Protein Kinase in Human Neutrophils." *J. Biol. Chem.*, vol. 267, No. 25, pp. 18122–18125 (1992).

Hasilik, A., "The Early and Late Processing of Lysosomal Enzymes: Proteolysis and Compartmentation," *Experientia* 48 Birkhauser Veerlag, CH–4010 Basel/Swizerland (1992).

Helminen, H.J., et al., "Quantitation of Lysosomal Enzyme Changes During Enforced Mdammary Gland Involution," *Exptl. Cell Res.* vol. 60, pp. 419–426 (1970).

Hoover, et al., Isolation of a Human Endothelial Cell Line from a Hepatic Angiocarcinoma, In Vitro 29A, 199–202 (1993).

Johnson, M.D., et al., "The Role of Cathespin D in the Invasiveness of Human Breach Cancer Cells," *Cancer Research*, vol. 53, pp. 873–877 (1993).

Kabat, H.A., et al., "Sequences of Proteins of Immunological Interest," 4th ed. (U.S. Dept. Health & Human Services, Bethesda, MD, 1987)*.

Kasai, M., et al., "Proenzyme Form of Cathepsin L Produced by Thymic Epithelial Cells Promotes Proliferation of Immature Thymocytes in the Presence of IL–1, IL–7, and Anti–CD3 Antibody," *Cellular Immunology*, vol. 150, pp. 124–136 (1993).

Klionsky, D.J. et al., "Intracellular Sorting and Processing of a Yeast Vacuolar Hydrolase: Proteinase A Propeptide Contains Vacuolar Targeting Information," *Molecular and Cellular Biology*, Vo. 8, No. 5, pp. 2105–2116 (1988).

Kornfeld, S., "Trafficking of Lysosomal Enzymes," FASEB J., vol. 1, pp. 462–468 (1987).

Kornfeld, S., "The Biogenesis of Lysosomes," *Ann. Rev. Cell Biol.*, vol. 5, pp. 483–525 (1989).

Larsen, L.B., et al., "Procathepsin D Cannot Autoactivate to Cathepsin D at Acid pH," FEBS Letters, vol. 319, Nos. 1, 2, pp. 54–58 (1993).

(List continued on next page.)

*Primary Examiner*—Lila Feisee
*Assistant Examiner*—Susan Ungar
*Attorney, Agent, or Firm*—Arnall Golden & Gregory, LLP

[57] ABSTRACT

Human procathepsin D was demonstrated to be mitogenic for breast cancer cells but not normal cells. The activation peptide of the procathepsin D appears to be responsible, since inhibition of enhancement of proliferation of breast cancer cells can be obtained by inhibition of the activation peptide through the use of an agent such as an antibody immunoreactive with the activation peptide.

5 Claims, 7 Drawing Sheets

PUBLICATIONS

Mathieu, M., et al., "Interactions of Cathepsin–D and Insulin–Like Growth Factor II (IGF–II) on the IGF–II/Mannose–6–Phosphate Receptor in Human Breast Cancer Cells and Possible Consequences on Mitogenic Activity of IGF–II)," *Mol. Endo.*, vol. 4, No. 9, pp. 1327–1335 (1990).

McIntyre, G.F., et al., "The Lysosomal Proenzyme Receptor that Binds Procathepsin L to Microsomal Membranes at pH 5 is a 43–kDa Integral Membrane Protein," *Proc. Natl. Acad. Sci. USA*, vol. 90, pp. 10588–10592 (1993).

McIntyre, G.F., et al., "The pH–Dependent Membrane Association of Procathepsin L is Mediated by a 9–Residue Sequence within the Propeptide," *J. Biological Chemistry*, vol. 269, No. 1, pp. 567–572 (1994).

McIntyre, G.F., "Procathepsins L and D are Membrane–Bound in Acidic Microsomal Vesicles," *J. Biological Chemistry*, vol. 266, No. 23, pp. 15438–15445 (1991).

Metcalf, P., et al., Two Crystal Structures for Cathepsin D: the Isysosomal Targeting Signal and Active Site, *The EMBO J.*, vol. 12, No. 4, pp. 1293–1302 (1993).

Morgan, D.O., et al., "Insulin–Like Growth Factor II Receptor as Multifunctional Binding Protein," *Nature*, vol. 329, pp. 301–307 (1987).

Myones, B.L., "Neutrophil and Monocyte Cell Surface p150.95 Has iC3b–Receptor ($CR_4$), Activity Resembling $CR_3$," *J. Clin. Invest.*, vol. 82, pp. 640–651 (1988).

Rijnboutt, S., et al., "Mannose 6–Phosphate–Independent Membrane Association of Cathepsin D., Glucocerebrosidase, and Spingolipid–Activating Protein in HepG2 Cells," *J. Biological Chemistry*, vol. 266, No. 8, pp. 4862–4868 (1991).

Rochefort, H., "Biological and Clinical Significance of Cathepsin D in Breast Center," *Acta Oncologica*, vol. 31, No. 2, pp. 125–130 (1992).

Ross, G.S., et al., "Identification of a C3bi–Specific Membrane Complement Receptor that is Expressed on Lymphocytes, Monocytes, Neutrophils, and Erythrocytes," *J. Exp. Med.*, vol. 155, pp. 96–110 (1982).

Sanchez, L.M., "Cathepsin D in Breast Secretions from Women with Breast Cancer," *Br. J. Cancer* vol. 67, pp. 1076–1081 (1993).

Stein, M., et al., "M, 46 000, Mannose 60–Phosphate Specific Receptor, Its Role in Targeting of Lysosomal Enzymes," *The EMBO J.* vol. 6, No. 9, pp. 2677–2681 (1987).

Vagner, J., et al., "Colour–Monitored Solid–Phase Multiple Peptide Synthesis under Low–Pressure Continuous–Flow Conditions, Synthesis of Medium–Size Peptides: The Propart of Human Procathepsin D and the Growth–Hormone Releasing Factor," *Coll. Czech. Chem. Commun.*, vol. 58, pp. 435–444 (1993).

Vaupel, P., et al., "Blood Flow, Oxygen and Nutrient Supply, and Metabolic Microenvironment of Human Tumors: A Review," *Cancer Research*, vol. 49, pp. 6440–6465 (1989).

Vetvicka, et al., "Effect of human procathepsin D on proliferation of human cell lines," *Cancer Letters*, 79,:131–135 (1994).

Vetvicka, V., et al., "Complement Factors H and I Synthesize by B Cell Lines Function to Generate a Growth Factor Activity from $C3^1$," *J. Immunology*, vol. 150, No. 9 (1993).

Vetvicka, V., et al., "Human Breast Milk Containing Procathepsin D–Detection by Specific Antibodies," *Biochemistry and Molecular Biology International*, vol. 30, No. 5, pp. 921–928 (1993).

Vignon, F., et al., "Autocrine Growth Stimulation of the MCF 7 Breast Cancer Cells by the Estrogen–Regulated 53 K Protein," *Endocrinology*, vol. 118, No. 4, pp. 1537–1544 (1986).

von Figura, K., "Molecular Recognition and Targeting of Lysosomal Proteins," *Current Opinion in Cell Biology*, vol. 3, pp. 642–646 (1991).

Westley, B.R., et al., "Oestrogen Regulates Cathepsin D mRNA levels in Oestrogen Responsive Human Breast Cancer Cells," *Nucleic Acids Research*, vol. 15, No. 9, pp. 3773–3786 (1987).

Williams, K.P., et al., "Isolation of a Membrane–Associated Cathespin D–Like Enzyme from the Model Antigen Presenting Cell, A20, and its Ability to Generate Antigenic Fragments from a Protein Antigen in a Cell–Free system," *Archives of Biochemistry and Biophysics*, vol. 305, No. 2, pp. 298–306 (1993).

Ferrandina, G., et al., "Cathespin D in Primary Squamous Laryngeal Tumors: Correlation with Clinico–Pathological Parameters and Receptor Status," *Cancer Letters*, vol. 67, 133–138 (1992).

Sacks, N.P.M., et al., "Cathepsin D Levels in Primary Breast Cancers: Relationships with Epidermal Growth Factor Receptor, Oestrogen Receptor and Axillary Nodal Status," *European J. of Cancer*, 29A(3):426–428 (1993) Note: European J. of Cancer is the correct cite not Int. J. Cancer.

Dillman, J. Clinical Oncology 12:1497–1515, 1994.

Gura, Science 270:575–7, 1995.

Harlow et al., "Antibodies A Laboratory Manual" Cold Spring Harbor Laboratory, 1988, pp. 285, 287.

Harris et al, Tibtech, 1993, 111:42–44.

Osband et al, Immunology Today, 1990, 11:193–195.

Hird et al, Genes & Cancer, Carney & Sikora, Eds 1990 John Wiley & Sons Ltd, pp. 183–189.

METHOD FOR INHIBITION OF BREAST TUMOR GROWTH

The United States government has rights in this invention by virtue of a grant from National Institutes of Health grant RO1 AI-27771-12 to Vaclav Vetvicka.

BACKGROUND OF THE INVENTION

The present invention is generally in the area of inhibition of breast cancer through manipulation of procathepsin D levels.

Cathepsin D (pCD) is an aspartic protease (EG 3.4.23.5) found in lysosomes of all mammalian cells, and is considered to be one of the main catabolic proteinases (Barret, (1970) Biochem. J. 117, 601–607). In the form of a zymogen, Cathepsin D is targeted via the mannose 6-phosphate (M6P) pathway, reviewed by Kornfeld and Mellman, (1989) Annu. Rev. Cell Biol. 5, 483–525. The two M6P receptors involved in the lysosomal targeting of pCD are localized both intracellularly and on the outer cell membrane. Two roles were identified for the cation-independent M6P receptor present on the cellular surface. The receptor recognizes molecules which contain the M6P tag and recaptures them (Stein et al (1987) EMBO J. 6, 2677–2681, and binds and mediates the effect of the insulin-like growth factor II (IGF II) (Morgan et al, (1987) Nature 329, 301–307).

Procathepsin D is secreted from cultured human cell lines at a low level. However, in response to estrogen stimulation, pCD becomes the major secreted protein in several human breast cancer cell lines, as reported by Vignon et al, (1986) "Autocrine growth stimulation of the MCF7 breast cancer cells by the estrogen-regulated 52 K protein" Endocrinology 118, 1537–1545; Westley and May, (1987) Nucleic Acids Res. 15, 3773–86; and Rochefort, (1992) "Biological and clinical significance of cathepsin D in breast cancer" Acta Oncologica 31, 125–130). Detailed analysis of the pCD gene regulating elements revealed a combination of both housekeeping and regulated promoter types, and suggested that pCD expression might also be controlled by estrogen under some physiological conditions as well (Cavailles et al, (1993) Proc. Natl. Acad. Sci. USA 90, 203–207). Increased levels of cathepsin D were previously detected during mammary gland involution in rats (Helminen and Ericson, (1970) "Quantitation of lysosomal enzyme changes during enforced mammary gland involution" Exp. Cell Res. 60, 419–426) and a steroid regulated production has been described in the rat uterus (Elangovan and Moulton, (1980) "Progesterone and estrogen control of rates of synthesis of uterine cathepsin D" J. Biol. Chem. 255, 7474–7479). The presence of intact pCD was reported in bovine (Larsen et al, (1993) FEBS Lett 319, 54–58) and human milk (Vetvicka et al, (1993) Biochem. Int. 30, 921–928).

The studies of pCD secretion from human breast cancer cell lines revealed that pCD acts as an autocrine mitogen (Rochefort 1992). The data on pCD mitogenic function support the postulated role of secreted pCD in tissue development and remodeling (Cavailles et al, 1993). Breast secretion from patients diagnosed with breast tumors contains significantly higher levels of procathepsin D than such secretions of healthy women, as reported by Sanchez, et al., (1993) "Cathepsin D in breast secretion from woman with breast cancer" Br. J. Cancer 67, 1076–1081. Procathepsin D levels are considered to be prognostic markers in human breast cancer Rochefort, H. (1992).

Nevertheless, there are clinical reports which doubt the significance of the prognostic value of cathepsin D concentrations, for example, by Johnson, et al., (1993) "The role of cathepsin D in the invasiveness of human breast cancer cells" Cancer Res. 53, 873–877. On the cellular level, Rochefort's group described the mitogenic effect of procathepsin D on human breast cancer cell line MCF 7 (Vignon, et al., (1986)), and later observations have shown that both procathepsin D and insulin-like growth factor II (IGF II) exhibit similar growth stimulation of this cell line (Mathieu, et al., (1990) "Interactions of cathepsin-D and insulin-like growth factor-II (IGF-II) on the IGF-II/mannose-6-phosphate receptor in human breast cancer cells and possible consequences on mitogenic activity of IGF-II" Mol. Endocrinol. 4, 1327–1335. The reported results are therefore confusing and it is unclear what role procathepsin D may play in normal and transformed tissues, nor whether procathepsin D is responsible for some differentiating factor present in breast tumor cells or is merely reactive.

In mammalian cells there are at least two mechanisms known for targeting pCD to lysosomes, as reported by Kornfeld, (1987) FASEB J. 1, 462–468. The recognition of newly synthesized pCD by phosphotransferase in the cis-Golgi, resulting in M6P labeling of oligosaccharides and subsequent capture by M6P receptors, is the predominant mode of lysosomal targeting. An alternative pathway has also been shown to operate in cells incapable of M6P labeling, reviewed by Kornfeld, 1987; and Glickman and Kornfeld, (1993) J. Cell Biol. 123, 99–108). In addition to the two proposed pathways of lysosomal targeting, there are several reports of M6P independent association of pCD with various intracellular membranes (Diement et al, (1988) J. Biol. Chem. 263, 6901–6907; McIntyre and Erickson, (1991) J. Biol. Chem. 266, 15438–15445; Rijnbout, et al, (1992) J. Biol. Chem. 266, 4862–4868, and Wliams and Smith, (1993) Arch. Biochem. Biophys. 305, 298–306). It was suggested that the activation peptides of lysosomal proteinases might be responsible for these interactions (von Figura, (1991) Curr. Opinion in Cell Biol. 3, 642–646). Grasel and Hasilik (1992) Biochem. Biophys. Res. Commun. 182, 267–282, identified a 60 KDa protein which is specifically associated with the pCD molecule.

The activation of the pCD is accomplished by the removal of the 44 amino acid activation peptide at the N-terminus of the proenzyme, and takes place at the low pH of lysosomes, reviewed by Hasilik, (1992) Experentia 48, 130–151. The activation is achieved by a combination of limited autoproteolysis and cleavage by other lysosomal proteinases. Cathepsin D is a proteinase with pH optimum close to 3, and its activity rapidly falls at pH above 5 (Bond and Butler, (1987) Annu. Rev. Biochem. 56, 333–364). Proteolytic activity of pCD in the extracellular space has not yet been reported. Nevertheless, tissues with high consumption of energy, as in the case of tumor tissues, may locally produce low pH (Vaupel et al, Cancer Res. 49, 6449–6465), and consequently allow the activation of a secreted pCD.

A role of the activation peptide in the M6P independent association of procathepsin L with intracellular membranes has been shown by McIntyre and Erickson, 1991, McIntyre and Erickson (1993) Proc. Natl. Acad. Sci. USA 90, 10588–10592, McIntyre et al (1994) J. Biol. Chem. 269, 567–572. The activation peptide of procathepsin L was also suggested to promote the proliferation of immature thymocytes (Kasai, et al, (1993) Cell. Immunol. 150, 124–136). The involvement of the activation peptides of aspartic vacuolar proteinase A from Saccharomyces cerevisiae in targeting to acidic vacuoles has been demonstrated by Klionsky et al, (1988) Mol. Cell. Biol. 8, 2105–2116. These data support the concept that the activation peptides of lysosomal proteinases have biologically significant functions other than only acting to inhibit lysosomal enzymes before they reach the lysosome, although it is not clear what these functions are.

It is therefore an object of the present invention to provide a method and reagents for inhibition of breast tumor proliferation and metastasis based on procathepsin D.

It is a further object of the present invention to provide an understanding of the role of cathepsin D activation peptide.

SUMMARY OF THE INVENTION

Human procathepsin D, isolated from the supernatant of human breast cancer cell line ZR-75-1, was tested for mitogenic activity for a broad spectrum of human-derived cell lines, as well as for the ability to regulate the expression of CD11a, CD11b, and CD62L receptors on human peripheral neutrophils and lymphocytes. These cell lines included: breast cancer cell lines ZR-75-1, MDA-MB-436, MBA-MD-483 and MDA-MB-231, B lymphoblastoid cell line Raji, the monocytoid cell line U937, T lymphoblastoid cell line 8402, epithelioid carcinoma cell line HELA, hepatocellular carcinoma cell line Hep G2, breast milk epithelial cell line HBL-100 and angiosarcoma cell line HAEND-1. Addition of procathepsin D to the cell lines significantly enhanced proliferation of breast cancer cell lines only.

Inhibition of procathepsin D by the use of anti-procathepsin D antibodies immunoreactive with the activation peptide significantly inhibits the proliferation of breast cancer cells. For nanomolar procathepsin D concentrations (0.1–2 nM), strong dose responsive cellular reactions were found employing both experimental designs. The results provide evidence that the mitogenic function involves the activation peptide of cathepsin D, which appears to be recognized by a surface receptor. The addition of antibodies raised against the activation peptide impaired the mitogenic activity of procathepsin D. A synthetic peptide corresponding to the activation peptide of procathepsin D produced similar effects to the zymogen molecule.

DETAILED DESCRIPTION OF THE INVENTION

The studies described in the following examples demonstrate that the mechanism of the mitogenic function of pCD is a function of the activation peptide, rather than a result of the proteolytic activity of activated extracellular cathepsin D, or of M6P residues of pCD carbohydrate groups binding to the M6P receptor. Experiments also demonstrate a pronounced activity of pCD in promoting the proliferation of a set of human cell lines and enhancing the surface receptor expression of human neutrophils and lymphocytes. In the experimental strategies, a dose-response dependence with saturation of the response signal was observed, indicating an interaction limited by the number of responding molecules. Three features of pCD were examined to determine the mechanism of these reactions which might be expected to be involved: existence of the propeptide, proteolytic activity, and presence of a M6P residues. Throughout the studies the addition of IGF II was used as a positive control for the interaction and activation of the cation-independent M6P receptor, because this receptor both transmits the signal of the IGF II and interacts with M6P residues present on the pCD structure (Mathieu et al, (1990) Mol. Endocrinol. 4, 1327–35).

The data show that the activation peptide of human pCD plays important role in the mitogenic function of pCD. Inhibition of this function by activation peptide specific antibodies and comparable activity of a synthetic activation peptide indicate existence of an interaction of the activation peptide with a surface receptor. This conclusion is supported by experiments on pCD association with cell surfaces, and inhibition of this association by the addition of the activation peptide. The mitogenic effect of this peptide, when used in fifty times higher molar concentration (20 nM), was very similar to that of isolated pCD. There was no activity detected when a peptide of the same size but with a scrambled sequence was used. Partial lower activity of the activation peptide of pCD in comparison to intact pCD may be explained by its higher conformational flexibility compared to the structure of the same region of pCD, or may be a result of its only forming a part of a three-dimensional signal present on the entire pCD structure. In the experiments, no inhibition of the mitogenic activity of pCD by pepstatin A (strong inhibitor of aspartic proteinases) was observed. When mature active cathepsin D was used in the experiments, no mitogenic effect was detected. Both results exclude the possibility of the involvement of cathepsin D proteolytic activity in pCD mitogenic functions.

Figure 5:
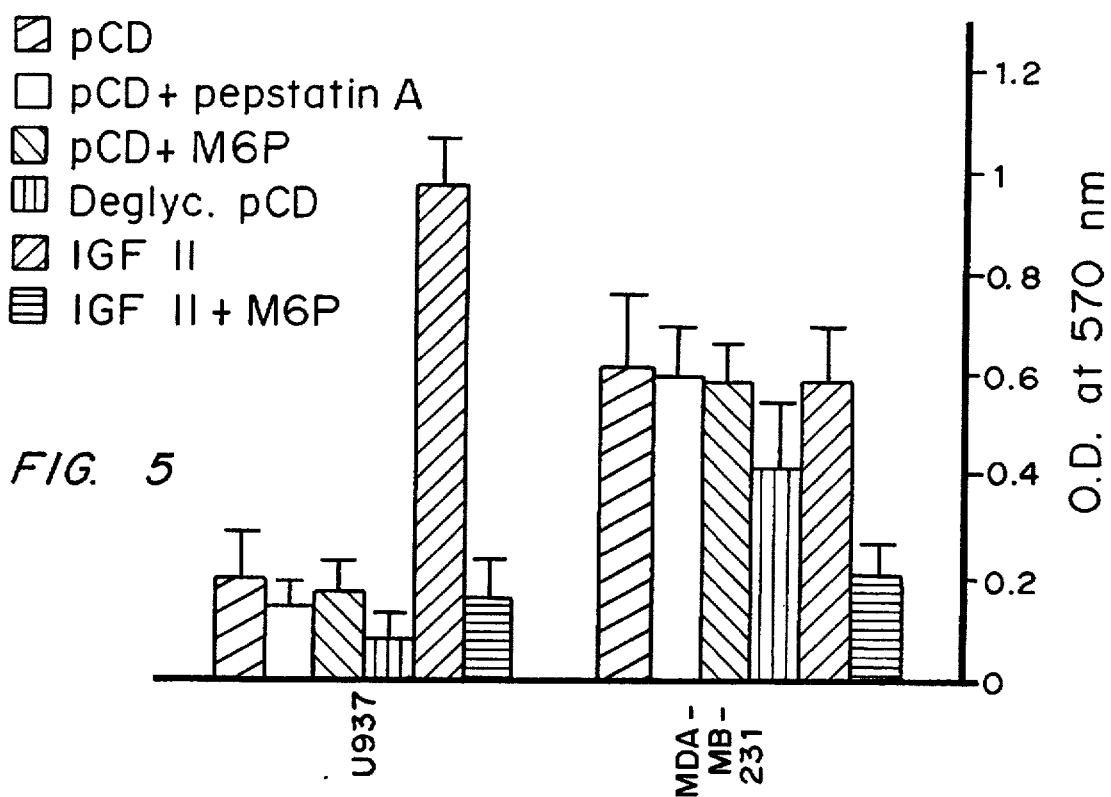
FIG. 5 is a bar graph showing the influence of additives or modification of pCD on the proliferative activity of pCD and IGF II in serum free medium for cell lines MDA-MB-231 and U937. The concentrations that were used were: pCD, 0.4 nM; M6P, 10 mM; pepstatin A, 1 µM; deglycosylated pCD (Deglyc.pCD), 0.4 nM.

Since high concentrations of M6P inhibit the interaction of the pCD with cell surface M6P receptors and block pCD internalization (Creek and Sly, (1984) in "Lysosomes in biology and pathology" Dingle, J. T., Dean, R. T. and Sly, W. E. (editors). Elsevier Science Publishers B. V., Amsterdam, pp. 63–82), if pCD mitogenic activity was realized through the M6P residues, then the addition of M6P would inhibit it. The experiments demonstrate that the addition of M6P had no influence on mitogenic activity of pCD (FIG. 5 and Table 2). Removing of the sugar moiety from the pCD structure slightly lowered the mitogenic activity of pCD in both proliferative and activation experiments. The addition of M6P, pepstatin A or the mixture used for the deglycosylation (with no pCD added) had no influence on the cellular growth when added to either no FCS or FCS supplemented media at the same concentrations as used above. The partial lowering of the activity may have several reasons. The deglycosylation of enzymes is often accompanied by some degree of disturbance of the original protein structure. Another possibility is that the interaction of the sugar moiety of pCD with the cell surface is important for the initial steps of pCD—cellular contacts. The removal of the sugar moiety would then slow down the initial binding steps, but would not abolish the activity. Over all the data show that the M6P sugar structures are not crucial for the mitogenic activity of pCD.

In conclusion, the data supports the mechanism that the mitogenic function of pCD relies on a specific structure of the activation peptide of pCD, and its interaction with a cell surface localized receptors. The findings identify the activation peptide of procathepsin D as a target for suppression of growth of certain breast tumors.

Inhibition of Proliferation of Breast Cancer Cells

Breast cancer cells proliferate on exposure to procathepsin D; the same effect can be obtained by exposure of the cells to the activation peptide defined in more detail below. Antibodies to the activation peptide portion of procathepsin D, peptides which inhibit binding to procathepsin D or activation peptide to breast cancer cells which induces an enhanced rate of proliferation, and other reagents which inhibit procathepsin D expression are effective in inhibiting proliferation of cells dependent on procathepsin concentrations.

Pharmaceutical Compositions

Antibodies to Activation Peptide

The antibodies are made and characterized below in the examples. These can be administered as fragments or humanized as follows to decrease immunogenicity.

Humanization of Antibodies

Because the methods for immunizing animals yield antibody which is not of human origin, the antibodies could elicit an adverse effect if administered to humans. Methods for "humanizing" antibodies, or generating less immunogenic fragments of non-human antibodies, are well known. A humanized antibody is one in which only the antigen-recognized sites, or complementarity-determining hypervariable regions (CDRs) are of non-human origin, whereas all framework regions (FR) of variable domains are products of human genes. These "humanized" antibodies present a lesser xenographic rejection stimulus when introduced to a human recipient.

To accomplish humanization of a selected mouse monoclonal antibody, the CDR grafting method described by Daugherty, et al., (1991) Nucl. Acids Res., 19:2471–2476, incorporated herein by reference, may be used. Briefly, the variable region DNA of a selected animal recombinant anti-idiotypic ScFv is sequenced by the method of Clackson, T., et al., (1991) Nature, 352:624–688, incorporated herein by reference. Using this sequence, animal CDRs are distinguished from animal framework regions (FR) based on locations of the CDRs in known sequences of animal variable genes. Kabat, H. A., et al., Sequences of Proteins of Immunological Interest, 4th Ed. (U.S. Dept. Health and Human Services, Bethesda, Md., 1987). Once the animal CDRs and FR are identified, the CDRs are grafted onto human heavy chain variable region framework by the use of synthetic oligonucleotides and polymerase chain reaction (PCR) recombination. Codons for the animal heavy chain CDRs, as well as the available human heavy chain variable region framework, are built in four (each 100 bases long) oligonucleotides. Using PCR, a grafted DNA sequence of 400 bases is formed that encodes for the recombinant animal CDR/human heavy chain FR protection.

The immunogenic stimulus presented by the monoclonal antibodies so produced may be further decreased by the use of Pharmacia's (Pharmacia LKB Biotechnology, Sweden) "Recombinant Phage Antibody System" (RPAS), which generates a single-chain Fv fragment (ScFv) which incorporates the complete antigen-binding domain of the antibody. In the RPAS, antibody variable heavy and light chain genes are separately amplified from the hybridoma mRNA and cloned into an expression vector. The heavy and light chain domains are co-expressed on the same polypeptide chain after joining with a short linker DNA which codes for a flexible peptide. This assembly generates a single-chain Fv fragment (ScFv) which incorporates the complete antigen-binding domain of the antibody. Compared to the intact monoclonal antibody, the recombinant ScFv includes a considerably lower number of epitopes, and thereby presents a much weaker immunogenic stimulus when injected into humans.

The antibodies can be formulated in standard pharmaceutical carriers for administration to patients in need thereof. These include saline, phosphate buffered saline, and other aqueous carriers, and liposomes, polymeric microspheres and other controlled release delivery devices, as are well known in the art. The antibodies can also be administered with adjuvant, such as muramyl dipeptide or other materials approved for use in humans (Freund's adjuvant can be used for administration of antibody to animals).

In vivo Immunization of Humans

The patient can also be immunized against the activation peptide of procathepsin D to achieve a similar inhibition of enhancement of proliferation that is obtained by administration to the patient of antibody. The activation peptide is not typically perceived as foreign by the patient.

Accordingly, it is preferably conjugated with or administered in combination with a carrier protein (such as bovine serum albumin) or a polysaccharide that increases its immunogenicity and prepared for injection by suitable methods known to those skilled in the art. For example, see E. A. Kabat, *Experimental Immunochemistry*, 2nd edition (Thomas 1971), incorporated herein by reference. Briefly, soluble antigens are generally sterilized by passage through a Chamberland, Berkefeld or Seitz filter having a pore size of 2 microns or less (Appropriate filters are also available from Costar, Cambridge, Mass. 02140). Suspensions of insoluble antigens may be sterilized by treatment with 0.2% formalin for several days in the cold or with 0.3 to 0.5% phenol. The antigen is then centrifuged off, washed once with sterile saline and suspended in saline. Phenol need not be removed. As a preservative for soluble as well as insoluble antigens 1% by volume of a 1% solution of methiolate is added.

For injection of humans with blood group substances, dextrans and pneumococcal polysaccharides, saline solutions of the desired concentration are prepared in 0.25% phenol; dextrans and the blood group substances may be autoclaved. Solutions of 1 mg per ml for the dextrans and blood group substances, and 0.05 mg per ml of the pneumococcal polysaccharides have been used. Sterility tests are carried out by streaking blood plates with 0.1 ml of solution and by inoculating samples into tubes containing 20 ml Difco thioglycollate broth. Plates and tubes are observed for ten days; no growth should occur.

Soluble proteins may be precipitated with alum to obtain an enhanced antibody response. To 100 ml sterile solution of the protein containing 1.5 mg of protein per ml, is added 5 ml of 1% sterile alum. This solution is then neutralized with 10N NaOH to maximum turbidity.

In one embodiment, 0.5 mg to 1.5 mg of antigen is injected into a human patient in a sufficient frequency to provoke the formation of anti-activation peptide antibodies.

Antisense Therapy

Other means to inhibit proliferation of cells induced by procathepsin D include gene therapy to block expression, using antisense to a nucleotide sequence encoding the activation peptide: LVRIPLHKFTSIRRTMSEVGGSV-EDLIAKGPVSKYSQAPAVTEG (amino acid sequence, Sequence ID No. 1) and derivatives thereof containing conservative substitutions which do not prevent hybridization between the antisense molecule and the target gene encoding procathepsin D activation peptide. The antisense molecules are preferably administered in a polymeric formulation or liposome formulation which has been demonstrated to greatly enhance uptake and half-life of the antisense molecules.

Peptides which Inhibit Binding

In still another embodiment, peptides derived from the activation peptide which bind to the receptor for the activation peptide of procathepsin D but which do not induce cell proliferation are used to block proliferation of cells induced by procathepsin D or activation peptide. The peptides are obtained by routine synthesis of peptides having the same sequence as activation peptide, making point mutations, screening for binding activity to breast cancer cells but not normal cells and then screening those that bind to determine efficacy in enhancing proliferation of the cells. The preferred peptide is that which then is determined to block inducement of proliferation of cells when the peptide is administered to breast cancer cells in combination with either procathepsin D or activation peptide.

The present invention will be further understood by reference to the following non-limiting examples. The following abbreviations were used: pCD, Procathepsin D; PPGN, pig pepsinogen; BCD, bovine cathepsin D; HCD, human cathepsin D; CD, cathepsin D; IGF II, insulin like growth factor II; mAb, monoclonal antibody; FCS, fetal calf serum; FITC, Fluorescein isothiocyanate; MTT, 3-(4,5-Dimethylthiazol-2-4)-2,5-diphenyltetrazolium bromide; PBS, 25 mM sodium phosphate, 150 mM NaCl, pH 7.2

EXAMPLE 1

Effect of Human Procathepsin D on Proliferation of Human Cell Lines

Materials and Methods

Chemicals

RPMI 1640 medium, β-estradiol, HEPES, MTT, human transferrin, MOPC-21 IgG and recombinant human insulin-like growth factor II were obtained from Sigma Chemicals (St. Louis, Mo.), Fetal Clone from Hyclone Laboratories (Logan, Utah), fetal bovine serum from Intergen (Purchase, N.Y.); Iscove's modified Dulbecco's medium from Whittaker (Walkersville, Md.).

Human Cell Lines

The B lymphoblastoid cell line Raji, the monocytoid cell line U937, epithelioid carcinoma cell line HELA, hepatocellular carcinoma cell line Hep G2 and breast milk epithelial cell line HBL-100 were obtained from the American Tissue Culture Collection (ATCC, Rockville, Md.). The human angiosarcoma cell line HAEND-1 was described by Hoover, et al., (1993) "Isolation of a human endothelial cell line from a hepatic angiocarcinoma" *In Vitro* 29A, 199–202. The T lymphoblastoid cell line 8402 was obtained from The Tissue Culture Facility of the Lineberger Cancer Research Center of the University of North Carolina at Chapel Hill, Chapel Hill, N.C. Human breast cancer cell lines ZR-75-1, MDA-MB-436, MBA-MD-483 and MDA-MB-231 were obtained from Dr. R. Ceriani of the John Muir Cancer and Aging Research Institute, Walnut Creek, Calif. The cancer cell lines were grown in RPMI 1640 medium with HEPES buffer supplemented with 10% (v/v) heat-inactivated Fetal Clone, 2 mM L-glutamine, 100 U/ml penicillin, and 100 μg/ml streptomycin in plastic disposable tissue culture flasks at 37° C. in a 5% $CO_2$/95% air incubator. All other cell lines were incubated in the same way except fetal clone was substituted with fetal bovine serum (FBS). In some experiments, secretion of procathepsin D was potentiated by addition of $10^{-8}$M β-estradiol.

Cell Cultivation

For growth experiments, cells were first incubated for two days in 0.1% FBS. The cells were harvested by centrifugation and washed six times in Iscove's modified Dulbecco's medium with HEPES buffer supplemented with glutamine, antibiotics and 10 μg/ml of human transferrin (Vetvicka, et al. (1993) "Complement factors H and I synthesized by B cell lines function to generate a growth factor activity from C3" *J. Immunol.* 150, 4052–4060). Cells were seeded in 96-well tissue culture plates at a density of $5 \times 10^4$ cells/ml (150 μl/well) in the presence or absence of different concentrations of purified procathepsin D, IGF II or various antibodies tested in triplicate wells. After 7 days in culture, 10 μl of MTT (5 mg/ml in PBS) was added to each well and the plates were cultivated for an additional 4 hr. The incorporation of MTT was stopped by the addition of 50 μl of 10% SDS in 0.01N HCl and the O.D. of the well supernatants was measured 24 hr later at 570 nm using Microplate Reader MR600 (Dynatech, Alexandria, Va.). All media were tested for endotoxin contamination and shown to contain less than 0.1 ng/ml LPS using the Limulus lysate test (E-TOXATE$_{nu}$, Sigma). Steroid-deprived cells were used in all experiments. The levels of procathepsin D in FBS at the concentration used were below detection level. Similarly, the levels of estrogens in FBS were less than or equal to 1 pg/ml. The experiments were repeated using both charcoal-treated FBS and medium without phenol red with identical results.

Isolation of Procathepsin D

Human procathepsin D was isolated from culture supernatants of human breast cancer cell line ZR-75. Briefly, a two step procedure was used. In the first step an immunoaffinity chromatography was used with anti-human cathepsin D activation peptide antibodies (Grinstein, S. W. (1992) "Chemoattractant-induced tyrosine phosphorylation and activation of microtubule-associated protein kinase in human neutrophils" *J. Biol. Chem.* 267(25), 18122–18125) attached to Protein A Sepharose. In the second step FPLC chromatography using Mono Q column and 20 mM Tris pH 7.2 were used.

Viability of Cells After Cultivation

The viability of cell lines was determined after 7 days of incubation using a Cyto-Tox 96™ cytotoxicity assay (Promega Corp., Madison, Wis.) according to the manufacturer instructions.

Results

Figure 1:
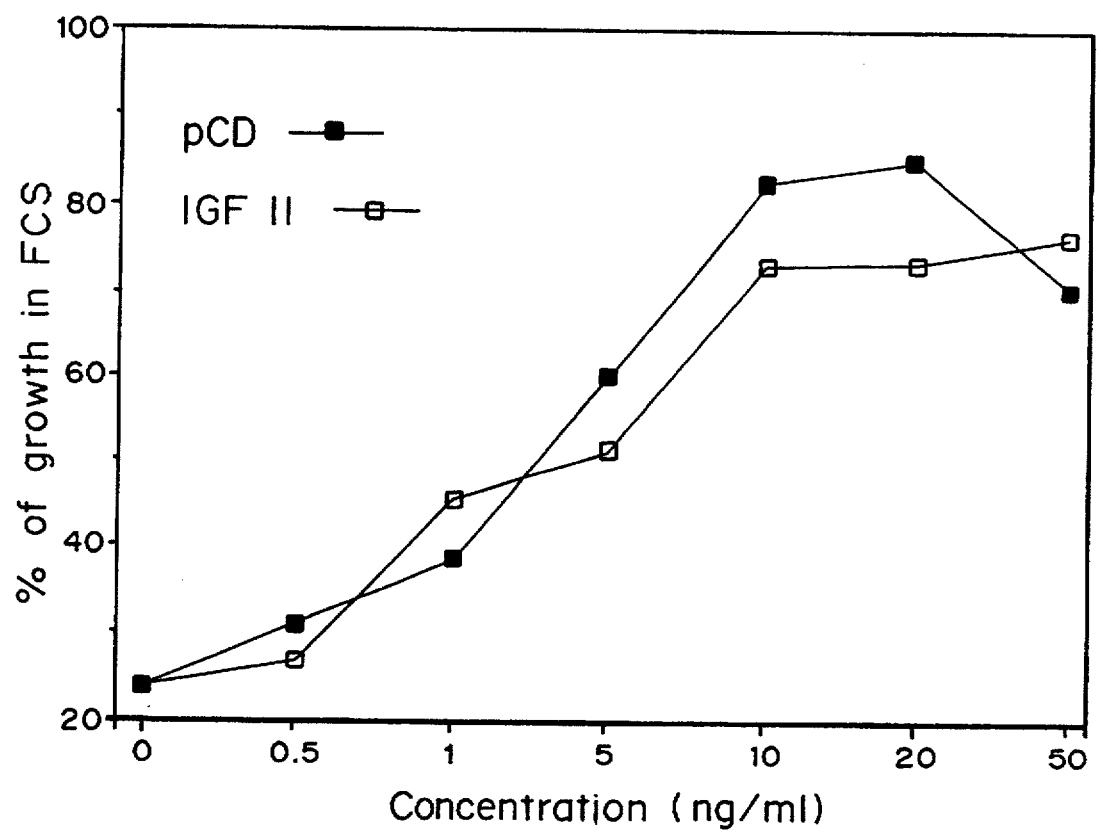
FIG. 1 is a graph of the effect of various concentrations (0, 0.5, 1, 5, 10, 20, and 50 ng/ml) of either procathepsin D (pCD) (closed squares) or IGF II (open squares) on the growth of human breast cancer cell line MDA-MB-231 in serum-free medium, measured as percent of growth in medium supplemented with FCS.
Figure 2:
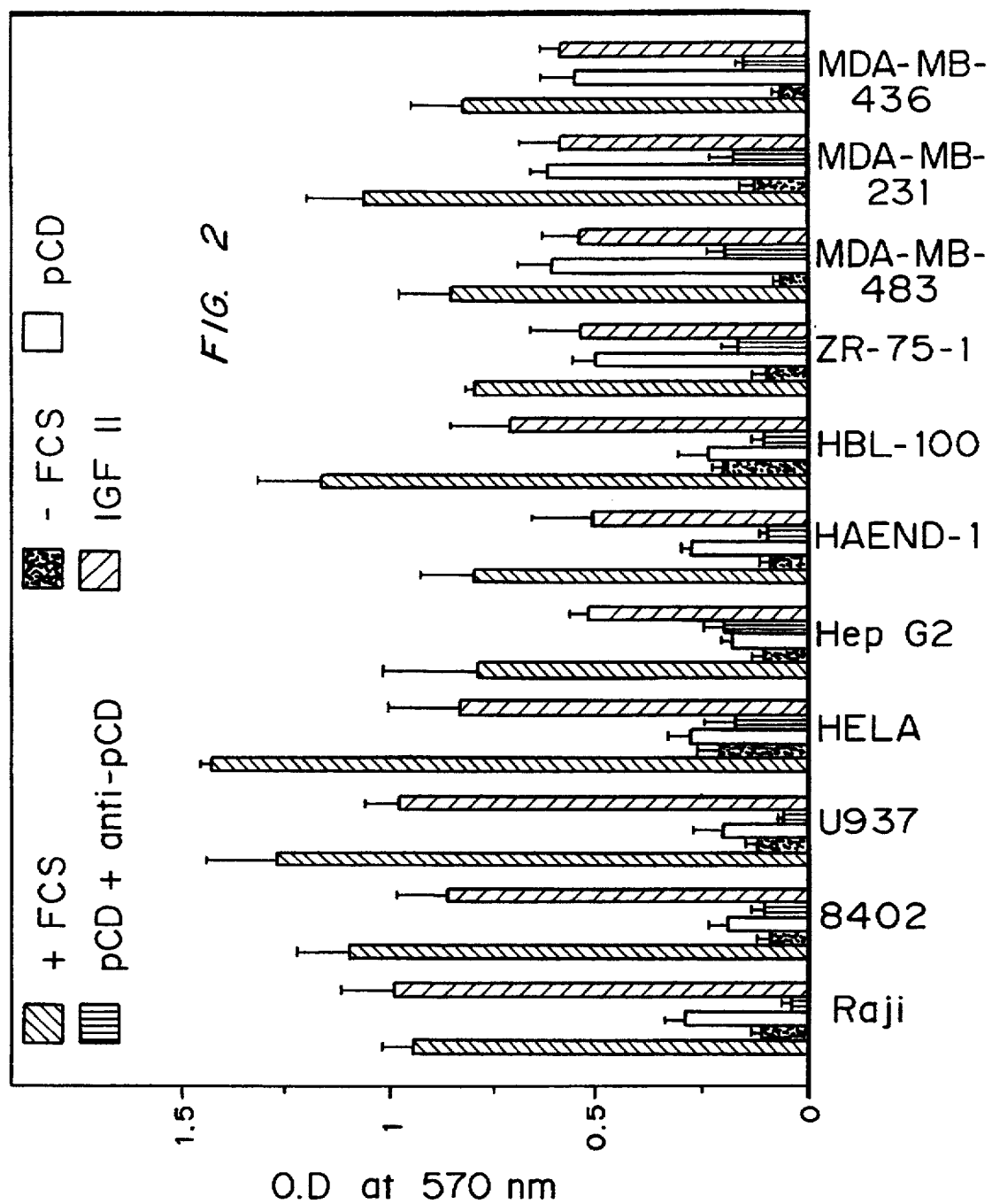
FIG. 2 is graph of the growth of human cell lines in serum-free medium containing procathepsin D (pCD), IGF II, or pCD and anti-pCD (10 ng/ml of either procathepsin D or IGF II). The results from growth in the control media supplemented with FCS (+FCS) are given for comparison. The results represent the mean±SD of three experiments.

The results showing the dose dependence of procathepsin D- or IGF II-mediated proliferation of breast cancer cells are summarized in FIG. 1. The results show the growth of MDA-MB-231 cell line, but identical results were found with other breast cancer cell lines. FIG. 2 shows the effect of 10 ng/ml of either procathepsin D or IGF II on proliferation of 11 different cell lines. Procathepsin D was shown to stimulate growth of all tested breast cancer cell lines (ZR-75-1, MDA-MB-483, MDA-MB-231 and MDA-MB-436). All other cell lines, with the exception of low growth stimulation of angiosarcoma cell line HAEND-1 which itself produces a low amount of procathepsin D, tested did not respond to the addition of procathepsin D. On the other hand, the same concentration of IGF II significantly stimulated the growth of all tested cell lines regardless of their type.

The results show that human procathepsin D has very strong proliferative activity restricted for cell lines derived from primary mammary tumors. Procathepsin D has this proliferative effect not only for cell lines which secrete this proenzyme under the influence of estrogens, such as ZR-75-1 or MCF7 cell lines, but also for those cell lines which do not possess the ability to secrete procathepsin D. The antibodies against procathepsin D block the proliferative effects of procathepsin D but not IGF II. This clearly shows the results are a specific function of procathepsin D and not a function of unidentified impurities.

EXAMPLE 2

Effect of Anti-Procathepsin D Antibodies on Cell Proliferation

Anti-procathepsin D antibodies raised against a synthetic peptide corresponding to the activation peptide of procathepsin D, as described by Vetvicka, et al., (1993) "Human breast milk contains procathepsin D—detection by specific antibodies" *Biochem. Molec. Biol. Int.* 20, 921–928, were tested for their effect on cell proliferation. These antibodies blocked the function of procathepsin D as shown in FIG. 2 and had no effect on the function of IGF II.

Figure 3:
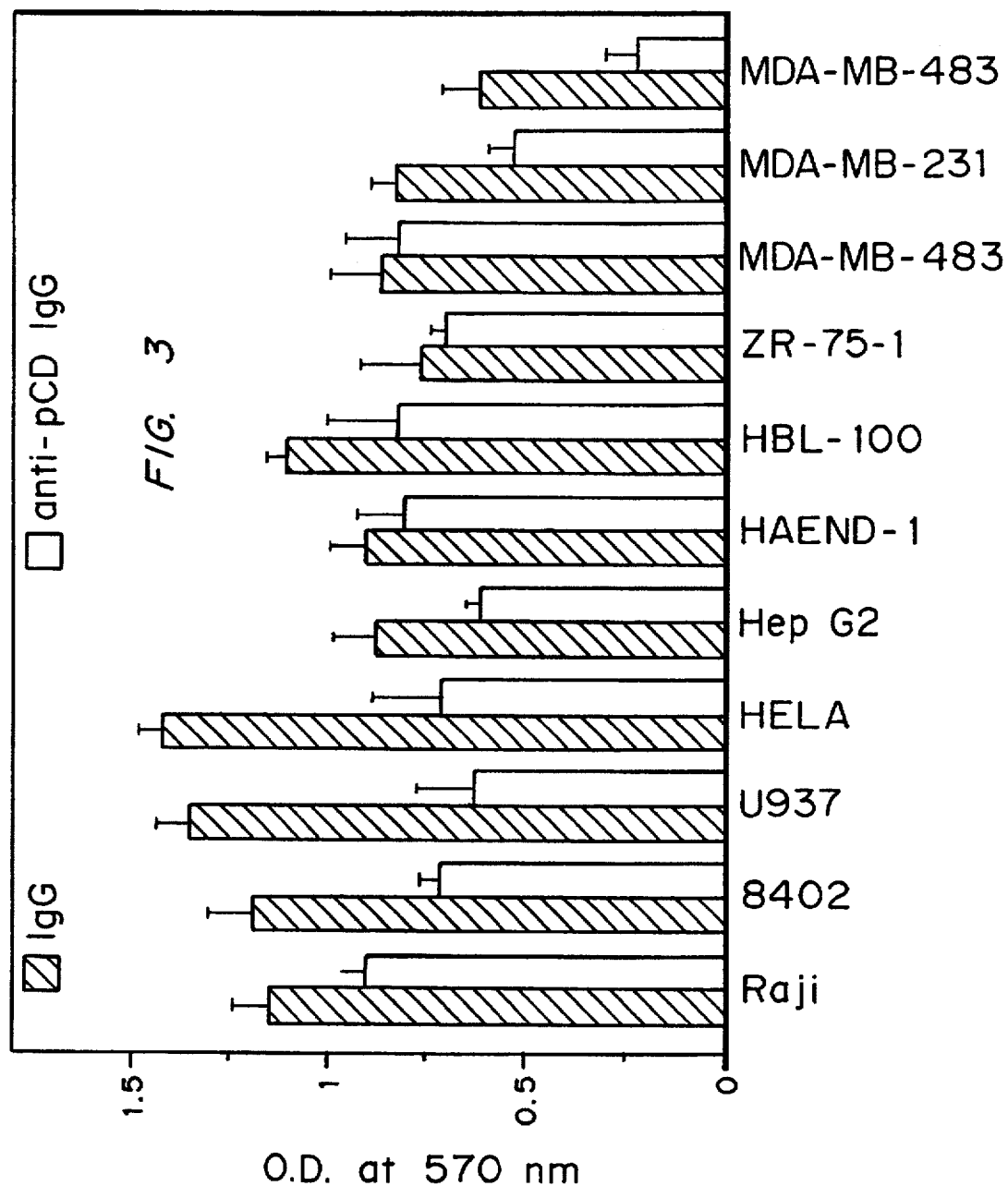
FIG. 3 is a graph of the inhibition of growth of human cell lines by anti-procathepsin D IgG (anti-pCD IgG). The results from growth in the control media with control MOPC-21 IgG (IgG) are given for comparison. The results represent the mean±SD of three experiments.

In simultaneous experiments, the effects of addition of anti-procathepsin D IgG on growth of a cell line in media supplemented with FCS was evaluated. Significant inhibition of growth was observed in two of the breast cancer cell lines (MDA-MB-231 and MDA-MB-436), as well as in cell lines 8402, U937, HELA and Hep G2, as shown in FIG. 3, which were resistant to the mitogenic effects of procathepsin D.

In order to show whether these antibodies inhibited the proliferation or killed the cells, the toxicity of parallel wells was measured by an enzymatic cytotoxicity assay. The data shown in Table 1 demonstrates that anti-procathepsin D IgG had no direct cytotoxic effect on any of the cell lines tested, but that the proliferation of these cell lines was merely blocked.

TABLE 1

Effect of anti-procathepsin D IgG on proliferation and death of cells.

| CELL LINE | PERCENTAGE OF DEAD CELLS | |
|---|---|---|
| | + anti-procathepsin D IgG | − anti-procathepsin D IgG |
| Raji | 3.7 | 5.2 |
| 8402 | 5.2 | 4.4 |
| U937 | 6.0 | 5.1 |
| HELA | 3.4 | 5.8 |
| Hep G2 | 6.7 | 6.0 |
| HAEND-1 | 2.3 | 2.8 |
| HBL-100 | 6.6 | 7.6 |
| ZR-75-1 | 5.0 | 5.3 |
| MDA-MB-483 | 9.6 | 8.1 |
| MBA-MB-231 | 5.9 | 3.4 |
| MDA-MB-436 | 8.3 | 6.4 |

Results represent mean data from 5 wells of one characteristic experiment.

The antibodies against procathepsin D were used in the experiments without the addition of procathepsin D. The suppression of proliferation was detected for several cell lines including those which had no response for procathepsin D addition. As the cytotoxicity experiments revealed, these antibodies did not have any cytotoxic effects on tested cell lines.

These in vitro experiments suggest that in vivo the presence of even a small population of procathepsin D-secreting cells might have a dramatic influence on the growth of surrounding tissues. This might explain why procathepsin D has not been correlated with the estrogen receptors, as reviewed by Rochefort, H. (1992) "Biological and clinical significance of cathepsin D in breast cancer" *Acta Oncologica* 31, 125–130, particularly as to those tumor cells which do not have high estrogen receptor levels, but are responsive to procathepsin D.

EXAMPLE 3

Mitogenic Function of Human Procathepsin D Activation Peptide and Inhibition of Cell Proliferation by Anti-Activation Peptide Antibodies The mechanism of the mitogenic function of pCD was studied by incubation of cells with pCD isolated from secretions of ZR-75-1 cell line. The cellular response was measured by monitoring of the cellular proliferation of different human cell lines, and by measuring the expression of several surface receptors on human peripheral neutrophils and lymphocytes. The results show that procathepsin D exhibited a mitogenic effect on cell lines derived from breast cancer tissues, and that its addition regulated the expression of several surface receptors on human leukocytes. The data further demonstrate that these mitogenic effects are mediated by the activation peptide of pCD, and do not involve pCD interaction via the mannose-6-phosphate group nor cathepsin D proteolytic activity. The data strongly suggest that there is a cell surface receptor that remains to be identified which is able to recognize the activation peptide of pCD.

The following materials and methods were used in Examples 3 and 4.

Materials and Methods

Reagents

N-glycanase was obtained from Genzyme (Cambridge, Mass.), pig pepsinogen was purchased from Worthington (Freeholf, N.J.), human cathepsin D was obtained from Biodesign (Kennebunk, Me.), human insulin-like growth factor II, bovine cathepsin D, bovine hemoglobin, RPMI 1640 and Iscove's modified Dulbecco's medium, β-estradiol, HEPES, propidium iodide, MTT and FITC were purchased from Sigma (St. Louis, Mo.). Ficoll-Hypaque and Fetal Clone were obtained from Hyclone Laboratories (Logan, Utah), pepstatin A was obtained from Serva (Heidelberg, Germany).

Antibodies

MN-41 IgG$_1$ anti-CD11b monoclonal antibody (mAb) (Eddy et al, (1984) Clin. Immunol. Imunopathol. 31, 371–389) and TS1/22 anti-CD11a were purified from ascites fluid as described by Myones et al, (1988) J. Clin. Invest. 82, 640–651. MOPC-21 myeloma IgG$_1$ was purchased from Sigma. CD62L mAb from Pharmingen (San Diego, Calif.) and affinity purified goat anti-mouse IgG-FITC from Southern Biotechnology Associates, Inc. (Birmingham, Ala.). Anti-pCD IgG antibodies (anti-pCD) were raised against a synthetic activation peptide of pCD, and the specificity for pCD ascertained. The anti-bovine cathepsin D IgG (anti-CD) antibodies were kindly provided by Dr. J. Tang, Oklahoma Medical Research Foundation, Oklahoma City, Okla.

Procathepsin D pCD was isolated from pooled media of cell line ZR-75-1 treated with 10 nM β-estrogen. Briefly, a two step procedure was employed using immunoaffinity chromatography based on anti-pCD antibodies followed by two anion exchange Mono Q FPLC separations at pH 7.2. The isolated pCD was free of contaminants as judged by SDS electrophoresis and other methods. The identity of the protein was confirmed by immunostaining on western-blots, and by blocking of the activity by pepstatin A. pCD before and after deglycosylation were analyzed by SDS electrophoresis, blotted, and visualized using pig anti-pCD IgG antibodies and rabbit anti-pig IgG antibodies conjugated with peroxidase. As an independent test of purity of the procathepsin D preparation, solutions of pCD were purified by reacting with the anti-CD antibodies bound to Protein A Sepharose™ (Pharmacia, Uppsala, Sweden).

Activation Peptide

The synthesis of the activation peptide of pCD was described by Vagner et al (1993) Coll. Czech. Chem. Commun. 58, 435–444. Briefly, peptide synthesis was accomplished by solid-phase multiple peptide synthesis under low-pressure continuous-flow conditions using a manually operated synthesizer. The synthesis was carried out in a flow reactor with adjustable volumen using $F_{moc}$/tBu protection strategy on standard methylbenzhydrylamine polystyrene-based resin. The purity of the peptide was confirmed by amino acid analysis using a Durrum 500 amino acid analyzer and by sequencing using an Applied Biosystems model 470A sequencer. The sequence is provided as Sequence ID No. 1.

Cell Lines

Human cell lines Hela, U937 (monocytoid) and Raji (B lymphoblastoid) were obtained from American Tissue Culture Collection (ATCC, Rockville, Md.). The 8402 cell line (T lymphoblastoid) was obtained from The Tissue Culture Facility of the Lineberger Cancer Research Center of the University of North Carolina at Chapel Hill, Chapel Hill, N.C. Human breast cancer cell lines ZR-75-1, MDA-MB-436 and MDA-MB-231 were obtained from Dr. R. Ceriani of the John Muir Cancer and Aging Research Institute, Walnut Creek, Calif. The cancer cell lines were grown in RPMI 1640 medium with HEPES buffer supplemented with 10% (v/v) heat-inactivated Fetal Clone, 2 mM L-Glutamine, 100 U/ml penicillin, and 100 gm/ml streptomycin at 37° C. in a 5% $CO_2$/95% air incubator. All other cell lines were incubated in the same way, except that the fetal clone was supplemented with fetal bovine serum (FCS).

Method for pCD Modifications

One microgram of pCD in 50 mM Tris-HCl buffer pH 7.5 was treated with 1 unit of N-glycanase for 16 hours at 37° C. The cleavage of oligosaccharides was confirmed by altered mobility on SDS electrophoresis. For FITC labeling, pCD (concentration 100 micrograms in 1 ml) was dialyzed against 100 mM borate buffer, pH 8.5. Twenty five mg of FITC were dissolved in 1 ml of dimethylsulfoxide and 20 μl of this solution was added to the dialyzed solution of pCD and incubated for 2 hours at room temperature. The solution was then dialyzed against 5 changes 50 mM Tris-HI buffer, pH 7.2.

Cellular Proliferation

Cells were first incubated for two days in 0.1% FCS and then were washed six times in Iscove's modified Dulbecco's medium and seeded into 96-well tissue culture plates at a density of $5 \times 10^4$ cells/ml (150 μ/well) with or without different amounts and types of additives. After seven days, 20 μl of MTT (5 mg/ml in PBS) was added to each well and the plates were cultivated for an additional 4 hours. The incorporation of MTT was stopped by the addition of 50 μl of 10% SDS in 0.01M HCl and the absorbance (optical density, OD) at 570 nm was measured 24 hours later using Microplate Reader MR600 (Dynatech, Alexandria, Va.).

Cell Staining and Flow Cytometry Analysis

Mononuclear cells and neutrophils from blood of normal healthy normal volunteers were separated by centrifugation on a two step (d=1.08 and 1.105) density gradient of Ficoll-Hypaque (Ross and Lambris, (1982) J. Exp. Med. 155, 96–110). The mononuclear cell fraction and neutrophil cell fraction were washed five times in RPMI-1640 medium and maintained in an ice bath until used. Cells were preincubated with appropriate amounts of tested substances for 30 minutes at 40° C. The cells were then washed once by centrifugation through a 3 ml cushion of 12% BSA in PBS with 10 mM sodium azide (12% BSA/PBS/azide). After removing the supernatants, the cells were incubated with 1 μg of goat-anti mouse IgG-FITC and 10 μl of propidium iodide (1 mg/ml in PBS) for another 30 minutes on ice. After washing once through a 3 ml cushion of 12% BSA/PBS/azide as described above, the cells were resuspended in PBS containing 1% BSA and 10 mM sodium azide. Flow cytometry was performed with an EPICS Profile II™ (Coulter Electronics Inc., Miami Lakes, Fla.), and the data obtained from greater than or equal to $10^4$ cells in each sample were stored in list mode. The binding of antibodies to polymorphonuclear cells and lymphocytes, gated by light scatter, was assessed by analyzing the stored list mode data with the Epics Elite Flow Cytometry Workstation software (Coulter).

Labeling of Cells with FITC-pCD $5 \times 10^5$ neutrophils were incubated with 50 ng of FITC-pCD for 30 minutes at 4° C. For the inhibition studies, the neutrophils were first incubated with 10 ng of the activation peptide. When the FITC labeled anti-pCD were used, the neutrophils was first incubated for 30 minutes with pCD and then incubated with the FITC labeled anti-pCD antibodies.

Sterile buffers and aseptic conditions were used at all steps. All media and buffers were tested for endotoxin contaminations, and shown to contain less than 0.1 ng/ml of endotoxin using the Limulus lysate test (E-TOXATE™, Sigma).

Results

Figure 4:
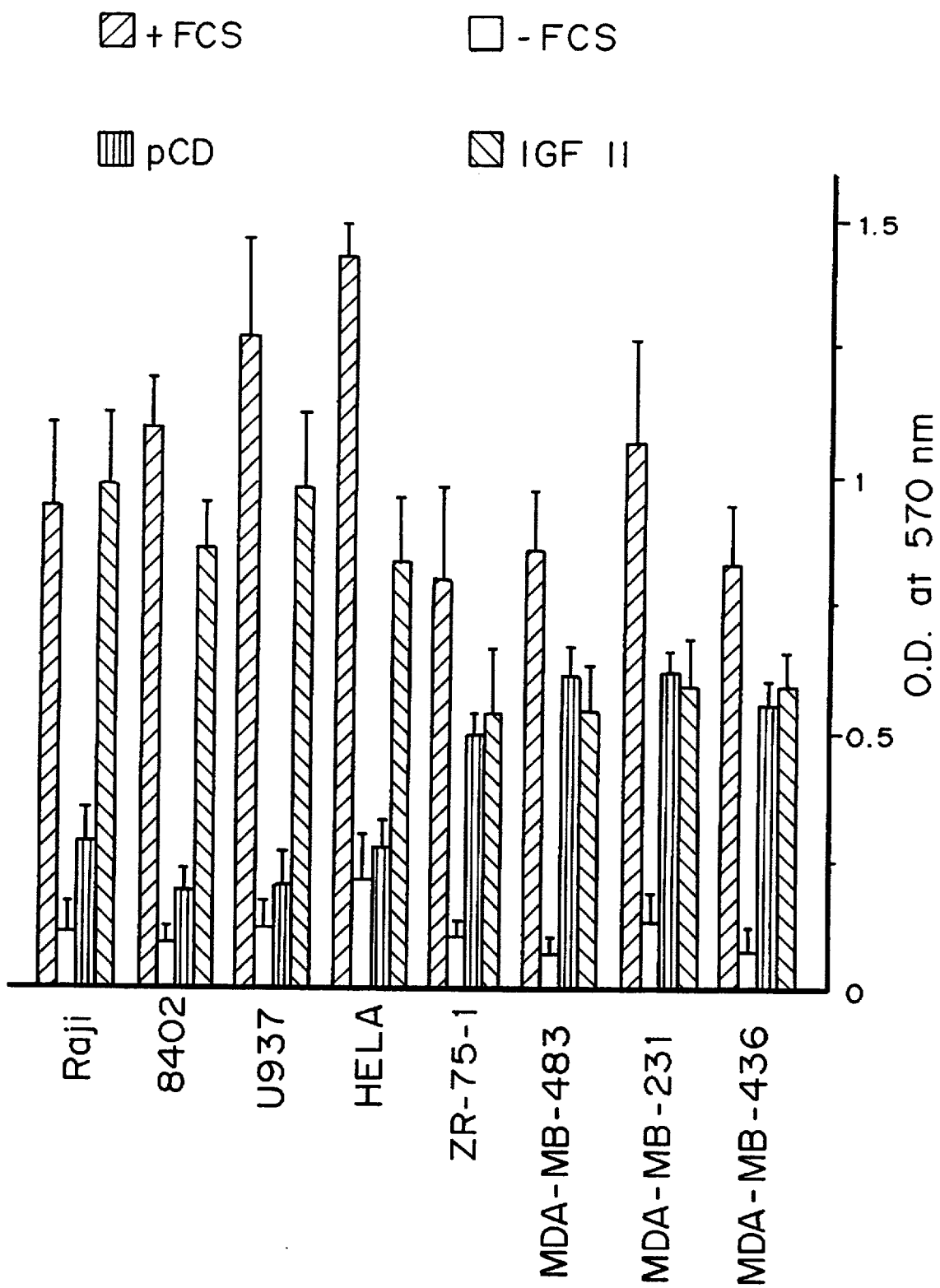
FIG. 4 is a bar graph of the growth of several human cell lines in serum-free medium containing either pCD or IGF II. The results from growth in control media supplemented with FCS (+FCS) are given for comparison. The concentration of pCD was 0.4 nM (20 ng/ml). The concentration of IGF II was 2.7 nM (20 ng/ml). The results in this experiment and in following proliferation experiments represent the mean±SD of five experiments.

Influence of pCD, IGF II, and pCD Derivatives on the Proliferation of Human Cell Lines FIG. 4 shows the effect of pCD and IGF II on the proliferation of cell lines ZR-75-1, MDA-MB-231, MDA-MB-436, Hela, Raji, U937 and 8402. The proliferation was measured by the incorporation of 3-(4,5-Dimethylthiazol-2-4)-2,5-diphenyltetrazolium bromide (MTT) by cells. The fetal calf serum (FCS) or IGF II supplemented media were used as positive controls. The proliferation of breast cancer cell lines was increased in the same way for both pCD and IGF II, while the cell lines which are not derived from breast cancer tissues responded to pCD much less than to IGF II. The proliferative activity of pCD and IGF II for breast cancer cell lines was dose responsive, as shown by FIG. 1. In subsequent proliferation experiments, the concentrations of pCD and IGF II were 20 ng/ml (0.4 nM for pCD and 2.7 nM for the IGF II). This experimental approach was used to study the mechanism of the mitogenic effect exhibited by pCD.

The influence of the addition of pepstatin A and M6P, together with the effect of deglycosylation of pCD are summarized in FIG. 5. Pepstatin A is a strong inhibitor of cathepsin D, with $K_i$ in the picomolar level, as reported by Baldwin et al, *Proc. Natl. Acad. Sci. USA* 90, 6796–6800, and was used to test the involvement of the proteolytic activity of cathepsin D on the observed mitogenic function. The hypothetical role of the M6P residues of PCD was investigated by either the addition of M6P or by the deglycosylation of pCD. The same set of cell lines was tested as in the studies shown in FIG. 4a. Since the results followed the same pattern, with strong reaction for breast cancer derived cell lines only, the results are shown for only two cell lines: 8402 as an example of nonresponding cell lines, and MDA-MB-231 as an example of strongly responding cell lines. These experiments showed that the addition of pepstatin A, M6P, or deglycosylation of pCD had very low influence on the observed proliferative activity of pCD. Nevertheless, high concentrations of M6P had a strong inhibitory influence on IGF II proliferative activity showing that, under these experimental conditions, strong interaction of M6P with the cation-independent M6P receptor occurs. These results indicated that the mitogenic function of pCD does not depend on the proteolytic activity nor on the presence of the M6P tag.

Figure 6:
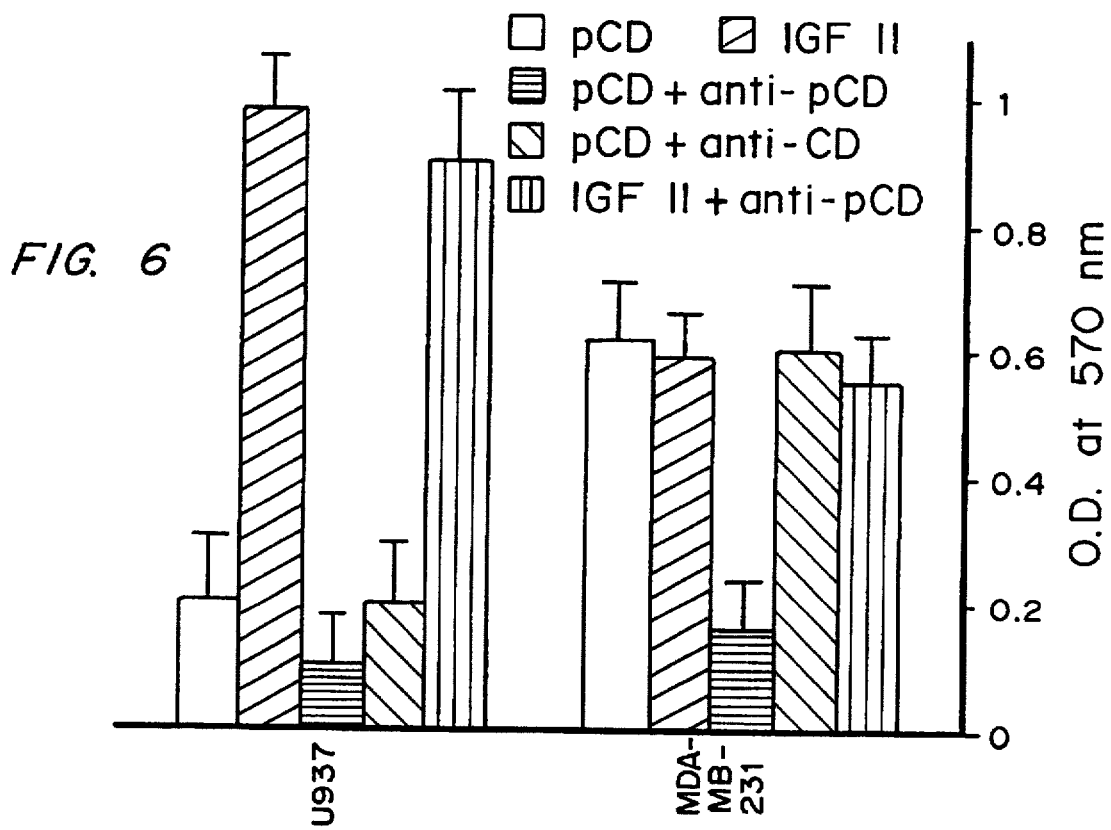
FIG. 6 is a bar graph showing the effect of two types of antibodies on the pCD or IGF II mediated proliferation of two human cell lines in serum free medium. The antibodies used were anti-procathepsin D (anti-pCD) and anti-cathepsin D (anti-CD) and their concentrations were 5 micrograms/ml of the IgG fraction.

A strong inhibition of the mitogenic function was observed when antibodies raised against the activation peptide of pCD were used, as shown by FIG. 6. These anti-pCD antibodies recognize epitopes contained within the activation peptide of pCD only, while anti-CD interact with epitopes of the mature enzyme and not with the activation peptide. The inhibition of the mitogenic effect observed for anti-pCD antibodies was specific for the pCD, and these antibodies had no effect on the function of IGF II. The anti-CD antibodies bound to Protein A Sepharose™ to remove the pCD from solutions prior to assaying the mitogenic activity was used as an additional control. No activity was detected in these controls. These experiments confirmed the purity of the preparation, and that the anti-pCD antibodies were specifically blocking the mitogenic activity of pCD. This result suggested the importance of the activation peptide of pCD in its mitogenic functions.

Figure 7:
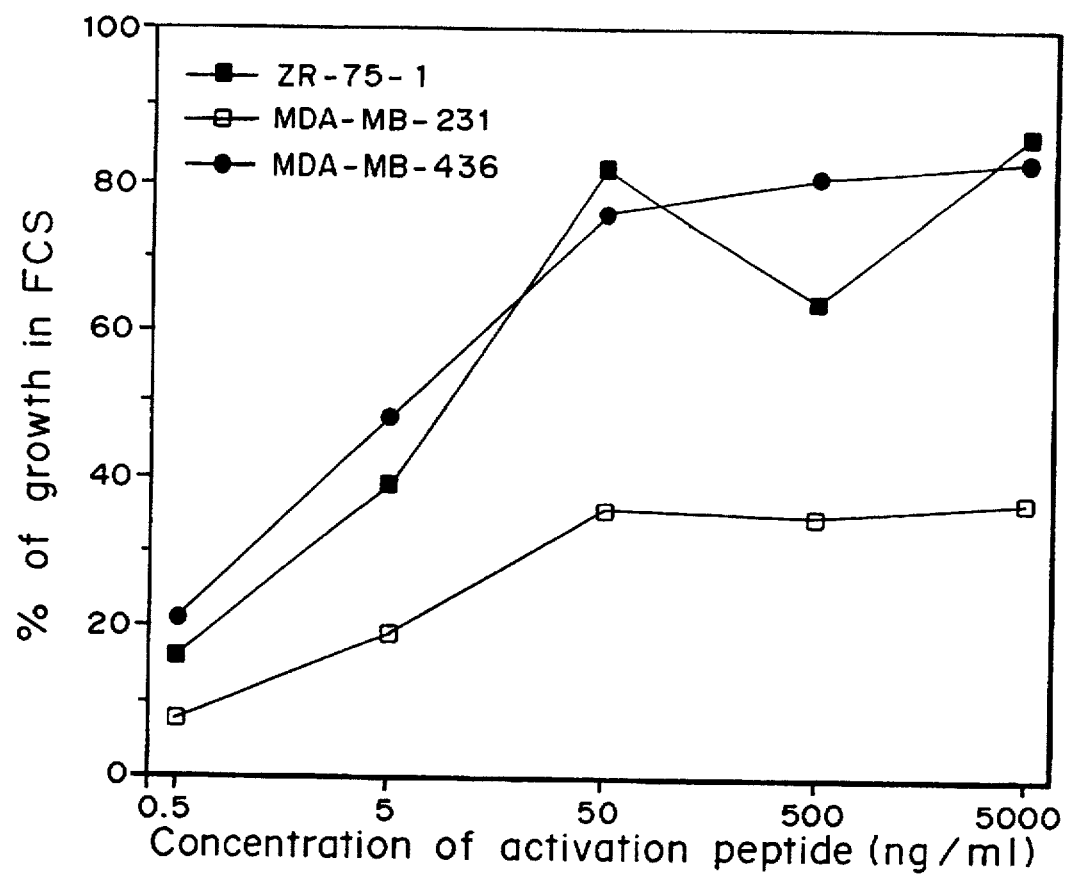
FIG. 7 is a bar graph comparing the influence of pCD (0.4 nM), IGF II (2.7 nM), bovine cathepsin D (BCD, 2 nM), human cathepsin D (HCD, 2 nM), the activation peptide of pCD (20 nM) and pig pepsinogen (PPGN, 20 nM) on the growth of four human cell lines in serum free medium.
Figure 8:
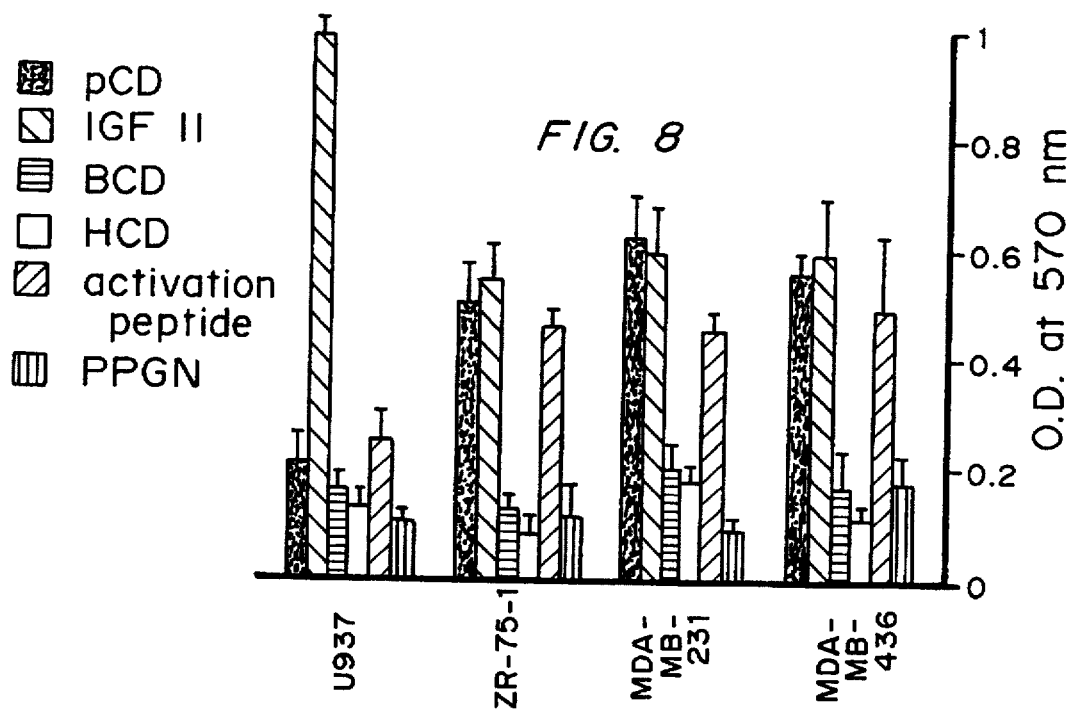
FIG. 8 is a graph of the dose response curves of the proliferative effect of the activation peptide for human breast cancer cell lines MDA-MB-231, MDA-MB-436 and ZR-75-1, measured as percent of growth in FCS versus concentration of activation peptide [ng/ml].

A synthetic peptide corresponding to the activation peptide of pCD was used to investigate further the role of the activation peptide in the mitogenic function. A dose responsive curve is shown in FIG. 7. Similar proliferative activity to that of pCD was observed, as shown by FIG. 8. The breast cancer derived cell lines responded in the same way to pCD and the synthetic activation peptide, while cell lines which did not react with pCD did not show any response to the peptide alone. No proliferative activity was observed for control molecules: pig pepsinogen (PPGN) or mature cathepsins D (FIG. 8). The PPGN control experiment was included for comparison with a protein of similar overall structure. Mature pepsin has a similar three-dimensional structure to cathepsin D (Metcalf and Fusek, (1993) *EMBO J.* 12, 1293–1302), but the sequences and the three-dimensional structures of the activation peptides of both enzymes differ substantially in the segment 43P—5 of pCD.

The influence of the addition of antibodies against cathepsin D on the mitogenic function of the activation peptide of pCD was also examined. Results were similar to that obtained for pCD. The function of the activation peptide was blocked by anti-pCD antibodies but not by the anti-CD antibodies. These results confirmed the hypothesis that the activation peptide of pCD plays important role in its mitogenic activity.

EXAMPLE 4

Figure 9A:
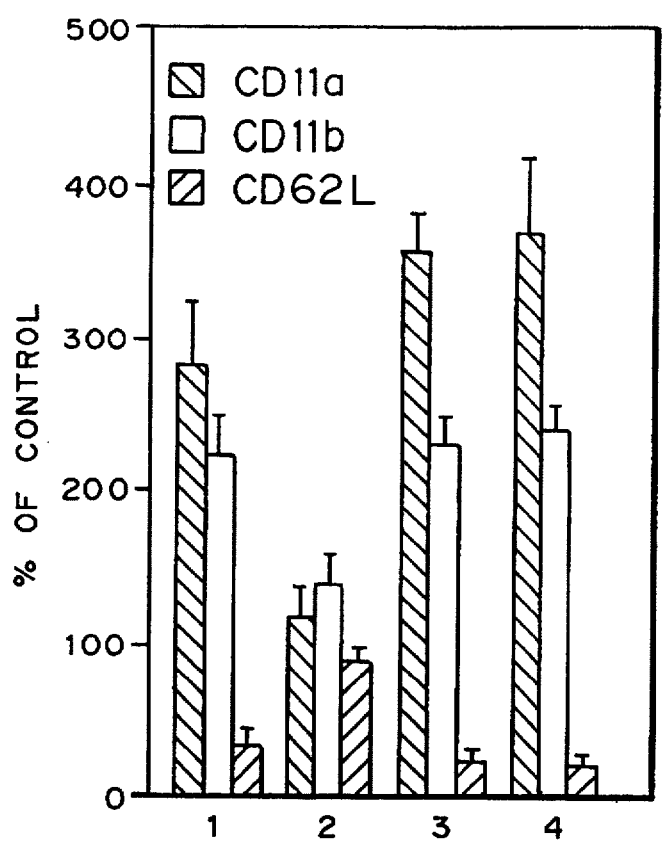
FIG. 9 is a graph of the regulation of three surface receptors (CD11b and CD62L) of human neutrophils (part A) and lymphocytes (part B) by pCD and IGF II. The number 1 stands for pCD (2 nM), number 2 for pCD (2 nM) with anti-pCD IgG (5 µg/ml), respectively. The data are compared to a control experiment where any additives were omitted and was taken as 100%. Results represents the mean±SD of five experiments.
Figure 9B:
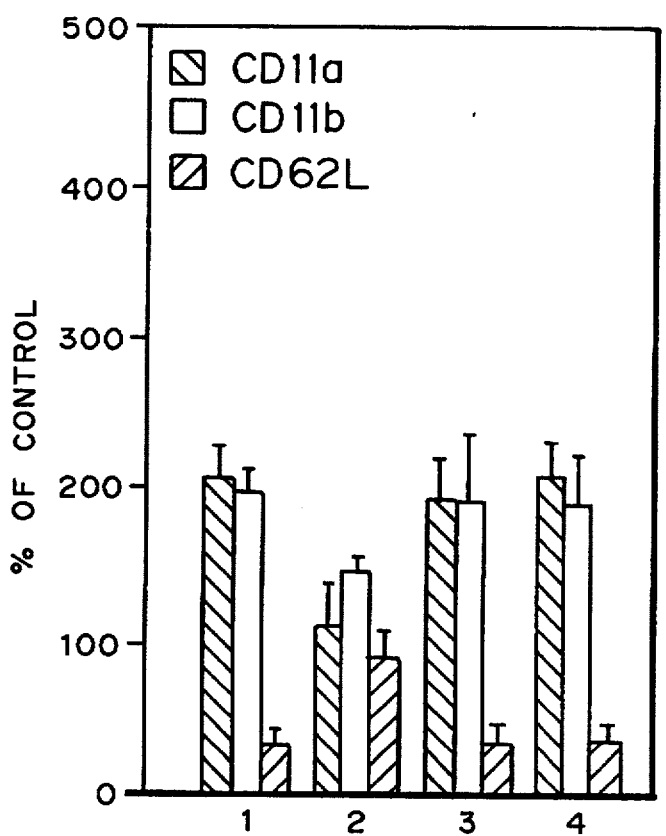

The Influence of pCD and IGF II on the Expression of Surface Receptors on Human Peripheral Neutrophils and Lymphocytes A second experimental approach in which the influence of the addition of pCD and its derivatives on the expression of surface receptors of human peripheral neutrophils and lymphocytes was examined was used to confirm the data from cellular proliferation experiments. The concentration of surface receptors CD11a, CD11b and CD62L were measured, as shown in FIG. 9. As a result of addition of pCD and IGF II, the CD11a and CD11b were upregulated while the CD62L was down regulated. The influence of the addition of anti-pCD antibodies on the activity of pCD and IGF II measured for neutrophil or lymphocyte associated receptors was also determined. The dose response curves for pCD (0.2–2 nM) and IGF II (0.5–3 nM) for the expression of both CD11b and CD62L were similar to that shown in FIG. 1.

The results obtained by this method using pCD, IGF II, pCD with pepstatin A or M6P, deglycosylated pCD, pCD preincubated with antibodies (anti-pCD or anti-CD), or the activation peptide of pCD, are summarized in Table 2. The effects on expression of the three cell surface receptors followed the same pattern as those obtained from the experiments measuring cellular proliferation: strong blocking by the anti-pCD antibodies, no inhibition with M6P or pepstatin A, and significant response to the synthetic activation peptide at concentration levels 10–100 nM.

pCD conjugated to a fluorescent marker (FITC) was used to demonstrate the interaction of pCD with human neutrophils and lymphocytes. 50 ng of FITC labeled pCD was incubated with 5×10⁵ cells in 100 μl for 30 minutes, or with the same amount of cells preincubated with 10 ng of the activation peptide and analyzed by flow cytometry. An 89% decrease in the intensity of the fluorescence signal (shift to the lower values of Log of Fluorescence) was observed when the activation peptide was added. When FITC labeled anti-PCD antibodies were added to cells preincubated with pCD, no fluorescence was observed. The fluorescent labeling of human neutrophils with pCD conjugated to FITC is inhibited at 89% by added activation peptide. In control experiments, the FITC-pCD conjugate was incubated with anti-pCD antibodies, and no labeling of antibodies was observed. Also, when non-labeled pCD was preincubated with neutrophils and then FITC-labeled anti-pCD antibodies were added, no staining was observed. Both these experiments support the importance of the activation peptide in the pCD—cellular interactions.

TABLE 2

Summary of flow cytometry experiments on activation of receptors on human leukocytes by pCD.

| Additive/ Receptor | CD11a | CD11b | CD62L |
|---|---|---|---|
| pCD | ++ | ++ | — |
| IGF II | ++ | ++ | — |
| pCD + pepstatin A | ++ | ++ | — |
| pCD + M6P | ++ | ++ | — |
| deglycosylated pCD | + | + | — |
| pCD + anti-pCD | 0 | 0 | 0 |
| pCD + anti-CD | ++ | ++ | — |
| IGF II + anti-pCD | ++ | ++ | — |
| anti-pCD | 0 | 0 | 0 |
| Activation peptide | ++ | ++ | — |
| Activation peptide + anti-pCD | 0 | 0 | 0 |

The sign "++" represents upregulation in the expression of a particular receptor, "—" means downregulation of a receptor, and "0" is no change in the concentration of a receptor in comparison to the control experiment. The concentrations of pCD was 2 nM, IGF II, 89 nM; M6P, 10 mM; pepstatin A, 1 μM; deglycosylated pCD, 2 nM; antibodies, 5 μg/ml; and activation peptide, 20 nM.

Modifications and variations of the present invention will be obvious to those skilled in the art from the foregoing. Such modifications and variations are intended to come within the scope of the appended claims.

We claim:

1. A method for inhibiting proliferation of breast cancer cells but not normal cells comprising administering to the cells antibodies that bind with cathepsin D activation peptide and which inhibit binding of procathepsin D activation peptide to the breast cancer cells in an amount effective to inhibit proliferation of the breast cancer cells.

2. The method of claim 1 wherein the antibodies are humanized antibodies which bind with the activation peptide of procathepsin D, which have complementarity-determining hypervariable regions of non-human origin and framework regions of variable domains of human genes.

3. A pharmaceutical composition for inhibiting proliferation of breast cancer cells but not normal cells comprising humanized antibodies, which have complementarity-determining hypervariable regions of non-human origin and framework regions of variable domains of human genes, wherein the antibodies bind with cathepsin D activation peptide and which block binding of procathepsin D to breast cancer cells and are in a pharmaceutically acceptable controlled release carrier for administration to a patient, in an amount effective to inhibit proliferation of breast cancer cells.

4. A method for inhibiting proliferation of breast cancer cells but not normal cells comprising administering to the cells procathepsin D activation peptides which bind to a receptor for procathepsin D activation peptide but do not stimulate proliferation of the cells, wherein the peptides are administered in an amount effective to inhibit proliferation of the breast cancer cells.

5. A pharmaceutical composition for inhibiting proliferation of breast cancer cells but not normal cells comprising procathepsin D activation peptides which bind to a receptor for procathepsin D activation peptide, wherein the peptides are in a pharmaceutically acceptable controlled release carrier for administration to a patient, in an amount effective to inhibit proliferation of breast cancer cells.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: YES ( v ) FRAGMENT TYPE: internal ( x i ) SEQUENCE DESCRIPTION: SEQ ID NO:1:

```
Leu  Val  Arg  Ile  Pro  Leu  His  Lys  Phe  Thr  Ser  Ile  Arg  Arg  Thr  Met
  1              5                        10                         15

Ser  Glu  Val  Gly  Gly  Ser  Val  Glu  Asp  Leu  Ile  Ala  Lys  Gly  Pro  Val
              20                        25                         30

Ser  Lys  Tyr  Ser  Gln  Ala  Pro  Ala  Val  Thr  Glu  Gly
             35                        40
```